US006312618B1

(12) United States Patent
Wu et al.

(10) Patent No.: US 6,312,618 B1
(45) Date of Patent: Nov. 6, 2001

(54) POLAR DIPHENYLDIACETYLENE LIQUID CRYSTALS

(75) Inventors: Shin-Tson Wu, Northridge, CA (US); Mary E. Neubert, Stow, OH (US)

(73) Assignee: HRL Laboratories, Mailbu, CA (US)

(*) Notice: Subject to any disclaimer, the term of this patent is extended or adjusted under 35 U.S.C. 154(b) by 0 days.

(21) Appl. No.: 09/541,735

(22) Filed: Apr. 3, 2000

(51) Int. Cl.$^7$ .................. C09K 19/06; C07C 43/205; C07C 43/285; C07C 25/24

(52) U.S. Cl. .................. 252/299.6; 558/411; 568/631; 568/661; 568/669; 570/127; 570/128

(58) Field of Search .................. 252/299.01, 299.6; 570/127, 128; 558/411; 568/631, 661, 669

(56) References Cited

U.S. PATENT DOCUMENTS

| 5,151,213 | 9/1992 | Reffenrath et al. . |
| 5,338,481 | 8/1994 | Wu et al. . |

OTHER PUBLICATIONS

CAPLUS 1992: 105809.*
Tray et al, SPIE 3421, pp. 142–150, 1998.

* cited by examiner

Primary Examiner—Shean C. Wu
(74) Attorney, Agent, or Firm—Tope-McKay & Associates; Gretchen E. Winter (57) ABSTRACT

A new class of asymmetric polar diphenyldiacetylene liquid crystal compounds and method for preparation are disclosed. The new class of liquid crystal compounds comprises the basic structure:

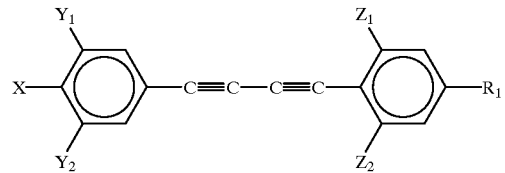

Wherein $R_1$ is an alkenyl group having the general formula $(C_2H_{2n-1})$, X is a cyano group, a fluoro group, $CF_3$, $OCF_3$, or a chloro group, $Y_1$ is unsubstituted, a fluoro group, a chloro group or a methyl group, $Y_2$ is unsubstituted, a fluoro group, a chloro group, or a methyl group, $Z_1$ is unsubstituted, a fluoro group, or a methyl group, and $Z_2$ is unsubstituted, a fluoro group, or a methyl group. The compounds disclosed exhibit high birefringence, low rotational viscosity, and have unexpectedly broad nematic ranges.

Also disclosed are eutectic mixtures comprising at least one polar diphenyldiacetylene having the general structure described above. The eutectic mixtures also have unexpectedly broad nematic ranges.

25 Claims, 2 Drawing Sheets

POLAR DIPHENYLDIACETYLENE LIQUID CRYSTALS

GOVERNMENT RIGHTS

At least a portion of the work related to the invention described herein was performed under government contract, specifically AFOSR contract #F49620-98-C-0019. All rights possessed by the U.S. Government in this subject matter are governed by the terms of that contract.

FIELD OF THE INVENTION

The present invention relates to liquid crystal materials and eutectic mixtures thereof. In particular, the invention is directed to a new class of diphenyldiacetylene liquid crystal compounds and eutectic liquid crystal mixtures with infrared and microwave applications.

BACKGROUND OF THE INVENTION

Nematic liquid crystals that have high birefringence, low viscosity, low threshold voltage, and are capable of maintaining the nematic phase over a broad temperature range are desirable in electro-optic phase and amplitude modulation applications such as infrared light valves and polymer-dispersed liquid crystal displays. High birefringence, or optical anisotropy (Δn), improves the efficiency of light modulation, and low rotational viscosity serves to shorten the response times. Low threshold voltage, which is inversely related to the dielectric anisotropy of the liquid crystal material, simplifies the electronics that drive the application.

Nematic diphenyldiacetylene liquid crystals as illustrated in Structure 1 have been shown to be useful electro-optic media for infrared and microwave modulation.

(Structure 1)

Typically, diphenyldiacetylene compounds have high birefringence and low rotational viscosity, and are particularly effective when used in eutectic mixtures. The importance of these properties is best summarized in the figure-of-merit parameter for the liquid crystal material, as shown in equation 1:

$$FM = \frac{K \Delta n^2}{\gamma_1} \quad (1)$$

wherein
FM is the figure-of-merit;
K is the elastic constant;
Δn is the optical anisotropy or birefringence; and
γ1 is the rotational viscosity of the compound.

Further improvement in these properties and broadening of the nematic phase range of these compounds would increase their utility in electro-optical and other liquid crystal applications.

The symmetry and polarity of diphenyldiacetylenes are critical to the overall properties of the resultant liquid crystal materials. Symmetrical diphenyldiacetylenes with both polar and non-polar side groups have been reported. [B. Grant, Mol. Cryst. Liq. Cryst. 48, 175 (1978); B. Grant et al, Mol. Cryst. Liq. Cryst. 51, 209 (1979)] However, in general, these liquid crystals exhibit higher melting temperatures (>80° C.) and large heat fusion enthalpy, narrow nematic phases, and small dielectric anisotropy, which render them undesirable for light modulation applications.

Asymmetrical diphenyldiacetylenes have also been reported. Non-polar asymmetrical diphenyldiacetylene compounds have been prepared as shown in Structure 2:

(Structure 2)

wherein $R_m$ is an alkyl group, an alkenyl group, an alkoxy group or an alkenoxy group and $R_n$ is an alkyl group, an alkenyl group, or an alkenoxy group [U.S. Pat No. 5,338,481]. Like the symmetrical diphenyldiacetylenes, these asymmetric compounds tend to exhibit high birefringence and low rotational viscosity. The asymmetric compounds generally have the additional benefit of a wide nematic range. However, the dielectric anisotropy of these materials tends to be quite low, which, as noted above, leads to a high threshold voltage for activating an LC device with these liquid crystal compounds.

Increasing the polarity of asymmetrical diphenyldiacetylene molecules is expected to increase their dielectric anisotropy. Diphenyldiacetylenes, as shown in Structure 3 below, with an alkyl, alkoxy, or alkenoxy side chain on one end ($R_{1'}$) and a fluoro side group at the other end have been prepared for this purpose. [Wu et al, Applied Physics Letters, 61, 2275 (1992) and 64, 1204 (1994); Opt. Eng. 32, 1792 (1993)]

(Structure 3)

In addition, asymmetric diphenyldiacetylenes with an additional polar substitutent on one of the phenyl groups as shown generally in Structure 4 below have been prepared:

(Structure 4)

For these diphenyldiacetylenes, $R_{1''}$ is an alkyl group, and X is a different alkyl group, an alkoxy group, a vinyl group, or a polar group such as cyano, chloro, or fluoro. When the Y position is substituted, it is either a fluoro or chloro group.

As expected, the dielectric anisotropy values for these compounds are about an order of magnitude higher than their non-polar asymmetric counterparts. However, the melting points of these compounds tend to be quite high and nematic ranges are also quite narrow, so the utility of these materials in liquid crystal applications is quite limited.

SUMMARY OF THE INVENTION

A new class of liquid crystal compounds is provided which has properties ideal to light modulation applications, particularly as components of eutectic mixtures. This new class of compounds is based on an asymmetrical diphenyldiacetylene structure with an alkenyl group on one end and a polar substituent on the other end, with optional additional polar side groups on the phenyl rings, as shown generally in Structure 5:

(Structure 5)

In this new class of compounds, $R_1$ is an alkenyl group having the general formula $(C_nH_{2n-1})$, X is a polar group, namely F, CN, $CF_3$, $OCF_3$, or Cl, $Y_1$ and $Y_2$ are independently H, F, Cl, or a methyl group, and Z is H, F, or a methyl group.

These new compounds, both as the pure material and as components of eutectic mixtures, have unexpectedly high figures of merit for use in light modulation applications. Furthermore, the nematic ranges of these compounds are also quite broad in comparison to their counterparts wherein $R_1$ is an alkyl group instead of an alkenyl group as outlined in the present invention.

DETAILED DESCRIPTION

The present invention relates to a new class of liquid crystal materials and eutectic mixtures thereof and a method for their synthesis. The following description is presented to enable one of ordinary skill in the art to make and use the invention and to incorporate it in the context of particular applications. It is anticipated that the invention may be tailored to a variety of other applications. Various modifications, as well as a variety of uses in different applications, will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

The present invention relates to polar, asymmetric diphenyldiacetylene liquid crystal compounds with the basic structure shown in Structure 5:

(Structure 5)

wherein $R_1$ is an alkenyl group of the general structure $(C_nH_{2n-1})$, X is a polar side group, namely F, CN, $CF_3$, $OCF_3$, or Cl, $Y_1$ and $Y_2$ are each either unsubstituted or a fluoro (F), chloro (Cl), or methyl ($CH_3$) group, and $Z_1$ and $Z_2$ is either unsubstituted or fluoro (F) or methyl ($CH_3$) group.

The $R_1$ alkenyl group preferably contains a double bond in the second position from the phenyl group, and thus has the general formula $(C_xH_{2x+1}CH=CH-CH_2-)$. In addition, this alkenyl side group has the general formula $(C_yH_{2y+1}CH=CH-(CH_2)-{}_{n-2-y})$, wherein n ranges from 2 to 12 and y ranges from 0 to 10.

In a first, preferred embodiment of the invention, as generally laid out in Structure 5, $R_1$ is an alkenyl side chain with a double bond in the second position, X is a fluoro group, and $Y_1$, $Y_2$, and Z are all unsubstituted. In this embodiment, the total carbon chain length for the alkenyl side chain is preferably 4, 5, or 6 carbons, and most preferably 4 or 5 carbons. The nematic range and figure-of-merit values for the resulting materials in this embodiment are unexpectedly high and are presented in Table I.

TABLE I

| Substituents | | | | Nematic | FM |
|---|---|---|---|---|---|
| n | X | T mp (° C.) | Tc(° C.) | range (° C.) | ($\mu m^2/S$) |
| 4 | F | 85.4 | 87.7 | 2.3 | |
| 4d2* | F | 93.3 | 164.8 | 71.5 | 95 @ 95° C. |
| 5 | F | 88.4 | 95.6 | 7.2 | |
| 5d2* | F | 91.6 | 163.0 | 71.4 | 90 @ 95° C. |
| 5d2* | F | 86.3 | 126.5 | 40.2 | |
| 5d2* | F | 69.0 | 91.2 | 22.2 | |
| 6 | F | 76.0 | 80.1 | 4.1 | |
| 6d2* | F | 82.0 | 149.2 | 67.2 | 50 @ 95° C. |
| 6d2* | FF | 78.9 | 117.2 | 38.3 | |
| 6d2* | FFF | 79.1 | 80.3 | 1.2 | | n = number of carbon atoms in the $R_1$ substituent as shown in Structure 5
*d2 = double bond in second position on substituent
X = substituent in X position as shown in Structure 5

For example, when the carbon chain in this embodiment is 4 carbons, the figure-of-merit for the resulting compound is the unexpectedly high value of 95 at 95° C. The nematic range of this material is about 71° C. By comparison, a similar compound wherein the alkenyl group is replaced by a 4-carbon alkyl chain has a nematic range of only 2.3° C. Similarly, when the carbon chain in the alkenyl side group of this embodiment contains 5 carbons, the resulting compound has an unexpected value of 90 at 95° C. and a nematic range of approximately 71° C. The comparable 5-carbon alkyl-substituted analog has a nematic range of only 7.2° C. Nematic ranges and figure-of-merit values of this and other embodiments of the present invention are presented along with the data for alkyl analogs in Table I.

Generally, the compounds in this first embodiment of the invention have unexpectedly high clearing temperatures, abbreviated $T_c$, a property which likely contributes to the unexpectedly high figure-of-merit values. As outlined in Wu, et al., Appl. Opt., 26, 3441 (1987) and demonstrated in Equation 2, the figure-of-merit value is increased by a higher clearing point:

$$FM \approx (1-T/T_c)^{0.75} \exp(-E/kT) \qquad (2)$$

Wherein

FM is the figure-of-merit;

T is the operating temperature;

$T_c$ is the clearing temperature;

k is the Boltzmann constant; and,

E is the activation energy of the rotational viscosity.

In other embodiments of this invention, both X and $Y_1$ or X, $Y_1$, and $Y_2$ as shown in Structure 5 are fluoro groups. In these embodiments, the alkenyl chain $R_1$ as described above preferably has a double bond in the second position, and contains 4, 5, or 6 carbons in the chain. Addition of the fluoro groups in the $Y_1$ position, and possibly also the $Y_2$ position, serves to decrease the melting point and increase the dielectric anisotropy relative to that of the first embodiment presented wherein X only is a fluoro group and the Y positions are unsubstituted. For example, when the $R_1$ alkenyl group is a 5-carbon chain and X is a fluoro group, addition of a second fluoro group in the $Y_1$ position reduces the melting point of the resulting liquid crystal material from 91.6° C. to 86.3° C.

Addition of a third fluoro group at the $Y_2$ position reduces the melting point to 69.0° C. These results are also shown in Table I above. The melting points are lower than that observed for the molecule with a 5-carbon alkyl chain in place of the alkenyl chain at the $R_1$ position. Furthermore, the nematic ranges of the difluoro and trifluoro compounds are appreciably wider, at approximately 40° C. and 22° C., respectively, compared to the alkyl variant, which has a nematic range of only 7.2° C.

In other embodiments of this invention, the homologues illustrated by Structure 5 are combined to create eutectic mixtures with high figures-of-merit. In these mixture embodiments, two or more of the compounds indicated by Structure 1, redrawn below:

(Structure 1)

are combined to form a mixture with improved figure-of-merit. Preferably, the compounds used have an alkenyl $R_1$ group with the double bond in the second position and containing 4 or 5 carbons as described previously. The preferred compounds additionally have a single fluoro group substitution at the X position and are unsubstituted at the $Y_1$, $Y_2$, and Z positions.

Figure 1:
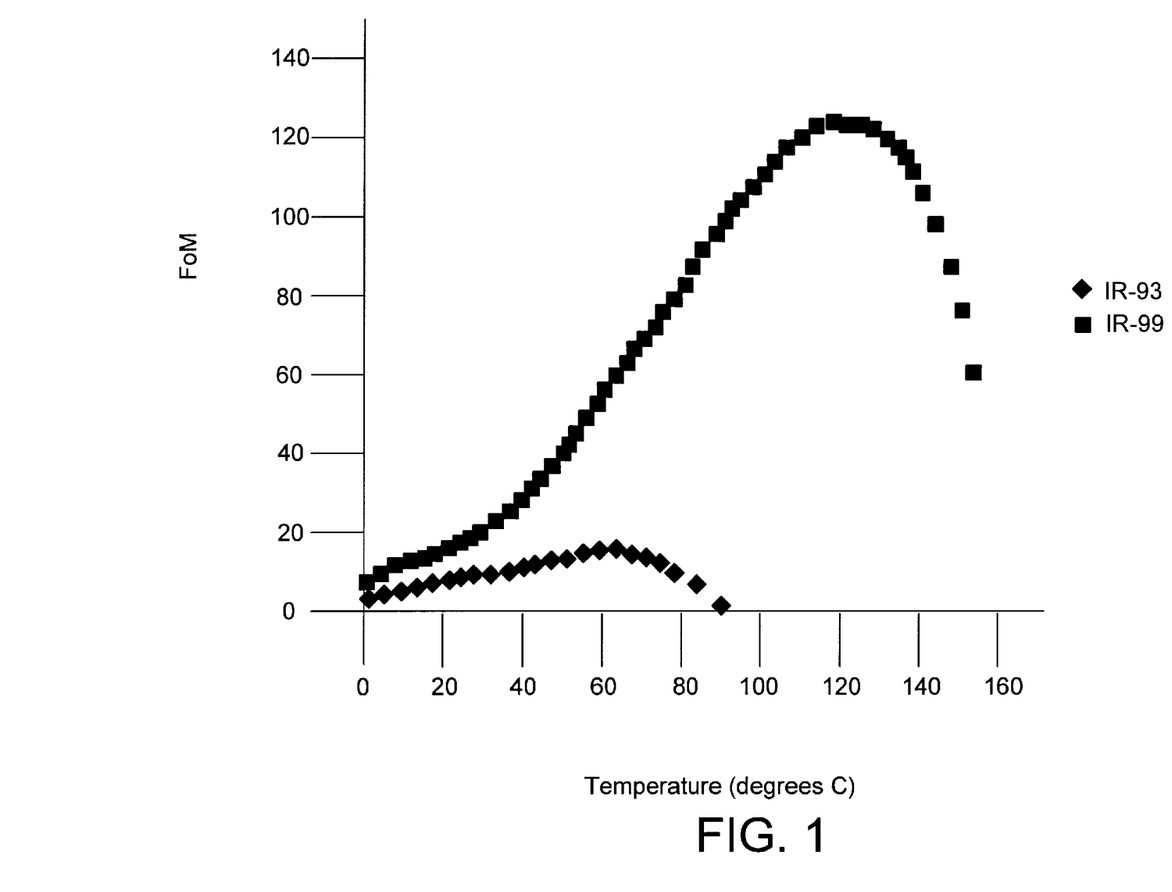
FIG. 1 is a plot comparing the figure of merit data for a mixture of alkyl-alkyl substituted and alkyl-fluoro diphenyldiacetylenes and a mixture of two polar diphenyldiacetylenes according to the present invention.

An example of the benefits of such a eutectic mixture is illustrated in FIG. 1, which shows the figure-of-merit plots for different eutectic mixtures of diphenyldiacetylene liquid crystal compounds. The mixture referred to as IR-93 in FIG. 1 is combination of previously developed diphenyldiacetylenes with the basic structures of Structure 2 and Structure 3 as redrawn below:

(Structure 2)

(Structure 3)

wherein $R_m$ and $R_n$ for Structure 2 and $R_{1'}$ for Structure 3 are all alkyl substitutents. This mixture reaches an optimal figure-of-merit value of about 20 at about 70° C.

Combining two homologues of the present invention as shown in basic Structure 5 produces a material with much higher figure-of-merit than the mixture IR-93. In the new material, 47% of the mixture is diphenyldiacetylene species wherein $R_1$ is a 4 carbon alkenyl substituent with the double bond in the second position as described above and X is a fluoro group. The remaining 53% of the new mixture is a diphenyldiacetylene wherein $R_1$ is a 5-carbon alkenyl substituent of the same type as the other component and X is a fluoro group. As shown in FIG. 1, this mixture, referred to as IR-99, exhibits an optimum figure-of-merit value of approximately 150 at about 120° C. Notably, this mixture additionally achieves comparably high figure-of-merit values at much lower temperature than the IR-93 mixture.

In yet other embodiments, homologues of the present invention as shown in the basic Structure 5 are combined with non-polar asymmetric diphenyldiacetylenes, as were disclosed in U.S. Pat. No. 5,338,481, and have the basic structure shown in Structure 2 wherein $R_m$ is either an alkyl group having the general formula ($C_mH_{2m+1}$), an alkoxy group having the general formula ($OC_mH_{2m+1}$), wherein m ranges from 1 to 12, an alkenyl group having the general formula ($C_mH_{2m-1}$), or an alkenoxy group having the general formula ($OC_mH_{2m-1}$) wherein m ranges from 1 to 12 and, $R_n$ is independently selected from the group consisting of an alkyl group having the general formula ($C_nH_{2n+1}$), an alkoxy group having the general formula ($OC_nH_{2n+1}$), wherein n ranges from 1 to 12, an alkenyl group having the general formula ($C_nH_{2n-1}$), and an alkenoxy group having the general formula ($OC_nH_{2n-1}$) wherein n ranges from 1 to 12; and m is not equal to n. As in the previous embodiment, homologues of the present invention used in the current embodiments, generally illustrated in Structure 5, preferably have a 4- or 5-carbon chain alkenyl $R_1$ group with the double bond in the second position as described above. The preferred compounds additionally have a single fluoro group substitution at the X position and are unsubstituted at the $Y_1$, $Y_2$, and Z positions.

Figure 2:
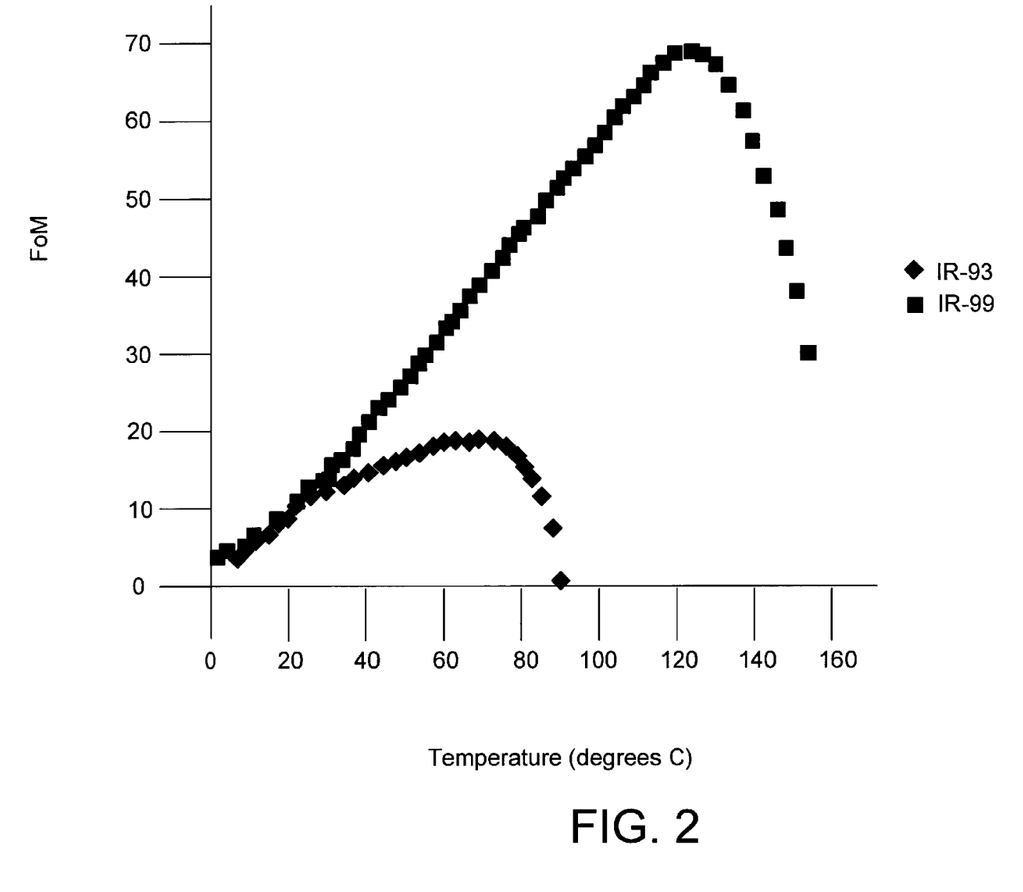
FIG. 2 is a plot comparing the figure-of-merit data for a mixture of alkyl-alkyl substituted and alkyl-fluoro substituted diphenyldiacetylenes and a mixture of several asymmetric non-polar diphenyldiacetylenes and polar diphenyldiacetylenes according to the present invention.

An illustration of such a mixture is provided in FIG. 2. As described in the previous embodiment, the mixture IR-93 in the figure is a combination of diphenyldiacetylenes as shown in Structures 2 and 3 wherein $R_m$, $R_n$ and $R_{1'}$ are all alkyl substitutents. This mixture reaches an optimal figure-of-merit value of about 20 at about 70° C. The mixture referred to as IR-97 in FIG. 2 is a combination of multiple preferred alkenyl-fluoro homologues of the present invention as shown in Structure 5 and also multiple non-polar asymmetric diphenyldiacetylenes as described above and shown in Structure 2. This mixture has a high optimal figure-of-merit of approximately 60 at about 100° C. and achieves improved figure-of-merit values versus the IR-93 mixture at temperatures of about 50° C. and higher.

A general procedure for the preparation of the embodiments of this invention is provided in Scheme 1. A detailed description of the synthesis according to Scheme 1 of the embodiment according to Structure 5 wherein $Y_1$, $Y_2$, $Z_1$, and $Z_2$ are H, X is a fluoro group, and $R_1$ is $CH_2CH=CHCH_2CH_3$ is also herein provided:

A stirred mixture of the alcohol I (n=1) (74.6 g, 0.37 mole) and $PBr_3$ (100.4 g, 0.37 mole) was heated at 170° C. for 20 min, cooled to room temperature then poured onto crushed ice (600 ml) and the resulting mixture extracted with $Et_2O$ (3×200 ml). The organic layer was separated, dried over anhyd $Na_2SO_4$ and filtered. The solvent was removed from the filtrate in vacuo to give 91.4 g (93.3%) of the dibromide II.

A mixture of the dibromide II (n=1) (91.6 g, 0.35 mole) and triphenylphosphine (91.9 g, 0.35 mole) was refluxed for 40 min, cooled to room temperature and added to $CH_2Cl_2$ (300 ml). This solution was added dropwise to vigorously stirred $Et_2O$ (21) at 5° C. over 2 hr. The resulting precipitate was collected by filtration and dried in vacuo. This crude salt III was pure enough to use in the next reaction (181.2 g, 99.3%).

To a stirred solution of the salt III (n=1) (87.8 g, 0.17 mole) in $CH_2Cl_2$ (1670 ml, dried over #4 A molecular sieves) at room temperature was added 18-crown-6 (2.20 g, 8.34 mmole). This mixture was refluxed for 5.0 min and then propionaldehyde (38.7 g, 0.67 mole) added dropwise. Refluxing was continued for 150 hrs and then the mixture was cooled to room temperature and filtered through a column of silica gel. The solvent was removed from the filtrate and the remaining material flash chromatographed on silica gel using hexane to give 26.2 g (69.9%) of the bromide IV.

To a stirred solution of the bromide IV (R=$CH_2CH_3$, n=1) (5.00 g, 22.2 mmole), 2-methyl-3-butyn-2-ol (4.67 g, 55.5 mmole), triphenylphosphine (139 g, 0.53 mmole), CuI (37 mg, 0.19 mmole) and $Et_3N$ (66.6 ml) under $N_2$ was added $Pd(PPh_3)_2Cl_2$ (37 mg, 0.05 mmole.) This mixture was heated at 60° C. for 30 min, refluxed for 3 hrs and then cooled to room temperature. The resulting precipitate was collected by filtration and washed thoroughly with $Et_2O$. The solvent was removed from the filtrate and remaining material dissolved in $Et_2O$. This solution was washed with $H_2O$(3×100 ml), dried over anhyd $NaSO_4$, filtered and the solvent removed from the filtrate in vacuo to give 6.37 g of the crude product. Chromatographed this material on silica gel using 50% hexane in $CH_2Cl_2$ gave 4.36 g (86.0%) of the protected acetylene V.

A mixture of the protected acetylene V (3.08 g, 13.5 mmole) (R=$CH_2CH_3$, n=1) and KOH (2.27 g, 40.5 mmole) in i-PrOH (45 ml) was refluxed for 22 hrs and then cooled to room temperature. The solvent was removed in vacuo and the remaining material dissolved in EtOAc. This solution was washed with $H_2O$, dried over anhyd $Na_2SO_4$ and filtered. The solvent was removed from the filtrate to give 2.34 g of the crude product. Flash chromatography of this material on silica gel with hexane gave 1.87 g (81.3%) of the liquid acetylene VI).

Bromoacetylene compounds VII were prepared using the methods already described in: H.-H. B Meng, L. R. Dalton and S.-T. Wu, Mol.Cryst. Liq. Cryst. 250, 303(1994), S.-T. Wu, D. J. M*9+argerum, H.-H. Meng and L. R. Dalton WO 94/03556 Feb. 17, 1994, and R. A. Shenoy, M. E. Neubert, D. G. Abdallah Jr, S. S. Keast and R. G. Petschek, Liq. Cryst, in press (2000). The synthesis of the bromoacetylenes is outlined in Scheme 2. Compounds X and VII are sensitive to light, air and heat. Reactions with these were carried out during daytime in hoods using no additional light sources. The reaction flasks were wrapped with aluminum foil. They were stored under argon in a refrigerator at ca. 15° C. The commercially available starting aldehydes IX were tested for acid impurity. When present, this was removed by an extraction with 5% KOH in $H_2O$ and distilled. Tertiary butanol was always distilled right before use. GC of the bromoacetylenes VII indicated these were at least 99.7% pure.

To a stirred mixture of CuCl (7.0 mg), propylamine (5.76 g, 97.4 mmoles) and the acetylene VI (R=$C_2H_5$, n=1) (4.65 g, 9.69 mmole) under $N_2$ at 0° C. was added $NH_2OH.HCl$ (470 mg, 6.82 mmole). This mix was stirred for 10 min and then a solution of the bromoacetylene VII (X=F, $Y_1$ and $Y_2$=H) (1.94 g, 9.75 mmole) in MeOH (56 ml) added dropwise within 90 min. Additional MeOH (100 ml) was added to facilitate stirring for 2.2 hrs. The resulting precipitate was removed by filtration, washed thoroughly with cold MeOH and dried. This material was dissolved in hexane (100 ml), washed with $H_2O$(50 ml), dried over $Na_2SO_4$ and filtered. The filtrate was filtered through silica gel. Removal of the solvent from the filtrate gave a solid that was recrystallized from $CH_3CN$ to give 1.31 g (46.6%) of the diacetylene VIII (X=F, $Y_1$ and $Y_2$=H, R=$CH_2CH_3$, n=1.

Scheme 1

-continued

V

↓ base

VI

VII

VIII

Scheme 2

IX

↓ PPh₃ catalyst

X

↓ t-BuO

VII

What is claimed is:

1. A diphenyldiacetylene liquid crystal compound comprising: the general structure of (Structure 5)

wherein
$R_1$ is selected from the group consisting of alkenyl groups having the general formula ($C_nH_{2n-1}$) wherein n ranges approximately from 2 to 12;
X is independently selected from the group consisting of $CN$, $F$, $CF_3$, $OCF_3$, and $Cl$;
$Y_1$ is independently selected from the group consisting of H, F, Cl, and $CH_3$;
$Y_2$ is independently selected from the group consisting of H, F, Cl, and $CH_3$;
$Z_1$ is independently selected from the group consisting of H, F, and $CH_3$; and,
$Z_2$ is independently selected from the group consisting of H, F, and $CH_3$.

2. A diphenyldiacetylene liquid crystal compound as set forth in claim 1, wherein $R_1$ is an alkenyl group having the general formula $C_mH_{2m+1}CH=CH-(CH_2)_{n-2-m}$, where n ranges approximately from 2 to 12, m ranges approximately from 0 to 10, and n−2−m is greater than or equal to 0.

3. A diphenyldiacetylene liquid crystal compound as set forth in claim 1, wherein $R_1$ is alkenyl group having the general formula $C_xH_{2x+1}CH=CH-(CH_2)-$, wherein x ranges approximately from 0 to 9.

4. A diphenyldiacetylene liquid crystal compound as set forth in claim 1, wherein X is a fluoro group (F), $Y_1$ is selected from the group consisting of H and F, $Y_2$ is selected from the group consisting of H and F, and $Z_1$ and $Z_2$ are H.

5. A diphenyldiacetylene liquid crystal compound as set forth in claim 1, wherein $R_1$ is an alkenyl group having the general formula $C_xH_{2x+}CH=CH-(CH_2)_2-$, wherein x ranges approximately from 0 to 8.

6. A eutectic mixture of liquid crystal compounds comprising at least two liquid crystal compounds including at least one diphenyldiacetylene liquid crystal compound having the general structure:

(Structure 4)

wherein
$R_1$ is selected from the group consisting of alkenyl groups having the general formula ($C_nH_{2n-1}$) wherein n ranges approximately from 2 to 12;
X is independently selected from the group consisting of $CN$, $F$, $CF_3$, $OCF_3$, and $Cl$;

$Y_1$ is independently selected from the group consisting of H, F, Cl, and $CH_3$;

$Y_2$ is independently selected from the group consisting of H, F, Cl, and $CH_3$;

$Z_1$ is independently selected from the group consisting of H, F, and $CH_3$; and $Z_2$ is independently selected from the group consisting of H, F, and $CH_3$.

7. A eutectic mixture as set forth in claim 6, wherein the mixture comprises two of the diphenyldiacetylene liquid crystal compounds.

8. A eutectic mixture as set forth in claim 6, wherein

X is a fluoro (F) group;

$Y_1$ is independently selected from the group consisting of H and F;

$Y_2$ is independently selected from the group consisting of H and F; and, $Z_1$ and $Z_2$ are H.

9. A eutectic mixture as set forth in claim 6, wherein the mixture comprises at least one of the diphenyldiacetylene liquid crystal compounds with the proviso that when X is CN, F, or Cl then $Y_1$, $Y_2$, and Z are not all H groups, and;

at least one of a second type of diphenyldiacetylene liquid crystal compound having the general structure:

(Structure 2)

wherein

$R_m$ is selected from the group consisting of an alkyl group having the general formula $(C_mH_{2m+1})$, an alkoxy group having the general formula $(OC_mH_{2m+1})$, an alkenyl group having the general formula $(C_mH_{2m-1})$, and an alkenoxy group having the general formula $(OC_mH_{2m-1})$ where m ranges approximately from 1 to 12; and, $R_n$ is independently selected from the group consisting of an alkyl group having the general formula $(C_nH_{2n+1})$, an alkoxy group having the general formula $(OC_nH_{2n+1})$, an alkenyl group having the general formula $(C_nH_{2n-1})$, and an alkenoxy group having the general formula $(OC_nH_{2n-1})$ wherein n ranges approximately from 1 to 12; and, n is not equal to m.

10. A method for preparing diphenyldiacetylene liquid crystal compounds, comprising the steps of:

i. reacting a brominated phenyl alcohol as shown in Structure I with a brominating agent to produce a dibromide as shown in Structure II:

(Structure I)

(Structure II)

wherein $Z_1$ on both structures is from the group consisting of H, F, and $CH_3$ and $Z_2$ on both structures is from the group consisting of H, F, and $CH_3$ and n ranges from 0 to approximately 10;

ii. isolating the dibromide of Structure II from the reaction of the brominated phenyl alcohol of Structure I and a brominating agent;

iii. reacting the dibromide of Structure II with triphenylphosphine to produce the tetraorganophosphonium salt shown in Structure III:

(Structure III)

wherein $Z_1$ is H, F, or $CH_3$, and $Z_2$ is H, F, or $CH_3$ and n ranges approximately from 0 to 10;

iv. isolating the salt of structure III from the reaction of the dibromide of Structure II with triphenylphosphine;

v. reacting the salt of structure III with an aldehyde having the formula RCHO wherein R is an alkyl substituent having the general formula $(C_xH_{2x+1})$ wherein x ranges from 0 to approximately 10, and a catalyst to produce the compound shown in Structure IV:

(Structure IV)

wherein $Z_1$ is from the group consisting of H, F, and $CH_3$, $Z_2$ is from the group consisting of H, F, and $CH_3$, R is an alkyl group having the formula $(C_xH_{2x+1})$ wherein x ranges from 0 to approximately 10, n ranges from 0 to approximately 10, and x+n is less than or equal to about 10;

vi. isolating the compound of Structure IV from the reaction of the salt of Structure III with and an aldehyde;

vii. reacting the compound of Structure IV with a protected 1-alkyne in the presence of a catalyst under an inert atmosphere to give the protected acetylene shown in Structure V:

(Structure V)

wherein $Z_1$ is H, F, or $CH_3$, $Z_2$ is H, F, or $CH_3$, R is an alkyl group having the formula $(C_xH_{2x+1})$ wherein x ranges from 0 to approximately 10, n ranges from 0 to approximately 10, and x+n is less than or equal to about 10;

viii. isolating the protected acetylene of Structure V from the reaction of the compound of Structure IV and a protected 1-alkyne in the presence of presence of a catalyst under an inert atmosphere;

ix. unprotecting the protected acetylene of Structure V with base to produce the acetylene shown in Structure VI:

(Structure VI)

wherein $Z_1$ is H, F, or $CH_3$, $Z_2$ is H, F, or $CH_3$, R is an alkyl group having the formula $(C_xH_{2x+1})$ wherein x ranges from 0 to approximately 10, n ranges from 0 to approximately 10 and x+n is less than or equal to about 10;

x. isolating the acetylene in Structure VI from the reaction of the acetylene of Structure V and base;

xi. reacting the benzaldehyde shown in Structure IX with triphenylphosphine and a catalyst to produce the bromostyryl compound shown in Structure X:

(Structure IX)

(Structure X)

wherein X is selected from the group consisting of CN, F, $CF_3$, $OCF_3$, and Cl, $Y_1$ is selected from the group consisting of H, F, and Cl, and $Y_2$ is selected from the group consisting of H, F, and Cl;

xii. isolating the dibromostyryl compound of Structure X from the reaction of Structure IX with triphenylphosphine and a catalyst;

xiii. reacting the dibromostyryl compound of Structure X with t-butoxide to produce the bromoacetylide shown in Structure VII;

(Structure VII)

wherein X is CN, F, $CF_3$, $OCF_3$, or Cl, $Y_1$ is H, F, or Cl, and $Y_2$ is H, F, or Cl;

xiv. isolating the bromoacetylide of Structure VII from the reaction of the dibromostyryl compound of Structure X and t-butoxide;

xv. reacting the acetylene of Structure VI with the bromoacetylide of Structure VII in the presence of a copper(I)salt and an amine in an inert atmosphere to produce the diacetylene shown in Structure VIII:

(Structure VIII)

wherein X is selected from the group consisting of CN, F, $CF_3$, $OCF_3$, and Cl, $Y_1$ is selected from the group consisting of H, F, and Cl, $Y_2$ is selected from the group consisting of H, F, and Cl, $Z_1$ is selected from the group consisting of H, F, and $CH_3$, $Z_2$ is selected from the group consisting of H, F, and $CH_3$, R is an alkyl group having the general formula $(C_xH_{2x+1})$ wherein x ranges from 0 to approximately 10, n ranges from 0 to approximately 10, and x+n is less than or equal to about 10;

xvi. isolating the diacetylene of Structure VIII from the reaction of the acetylene of Structure VI with the bromoacetylide of Structure VII in the presence of a copper(I) salt and an amine in an inert atmosphere.

11. A method for preparing diphenyldiacetylene liquid crystal compounds as set forth in claim 10 wherein the brominating agent in step i is tribromophosphine.

12. A method for preparing diphenyldiacetylene liquid crystal compounds as set forth in claim 10 wherein the brominating agent in step i is hydrobromic acid.

13. A method for preparing diphenyldiacetylene liquid crystal compounds as set forth in claim 10 wherein $Z_1$ and $Z_2$ on the brominated phenyl alcohol shown in Structure I in step i are both H.

14. A method for preparing diphenyldiacetylene liquid crystal compounds as set forth in claim 10 wherein the value "n" on the brominated phenyl alcohol shown in Structure I in step i is equal to 2.

15. A method for preparing diphenyldiacetylene liquid crystal compounds as set forth in claim 10 wherein the aldehyde in step v is propionaldehyde.

16. A method for preparing diphenyldiacetylene liquid crystal compounds as set forth in claim 10 wherein the catalyst in step v is 18-crown-6.

17. A method for preparing diphenyldiacetylene liquid crystal compounds as set forth in claim 10 wherein the protected alkyne in step vii is 2-methyl-3-butyn-2-ol.

18. A method for preparing diphenyldiacetylene liquid crystal compounds as set forth in claim 10 wherein the catalyst in step vii is comprised of $Pd(Ph_3P)_2Cl_2$, $PPh_3$, $Et_3N$, and CuI.

19. A method for preparing diphenyldiacetylene liquid crystal compounds as set forth in claim 10 wherein the inert atmosphere in step vii is an $N_2$ atmosphere.

20. A method for preparing diphenyldiacetylene liquid crystal compounds as set forth in claim 10 wherein the base in step ix is potassium hydroxide.

21. A method for preparing diphenyldiacetylene liquid crystal compounds as set forth in claim 10 wherein the catalyst in step xi is comprised of carbontetrabromide and zinc metal.

22. A method for preparing diphenyldiacetylene liquid crystal compounds as set forth in claim 10 wherein X on the bromoacetylide shown in Structure VII is a fluoro group and $Y_1$ and $Y_2$ on the bromoacetylide are each independently selected from the group consisting H and F.

23. A method for preparing diphenyldiacetylene liquid crystal compounds as set forth in claim 10 wherein the copper(I) salt in step xv is CuCl.

24. A method for preparing diphenyldiacetylene liquid crystal compounds as set forth in claim 10 wherein the amine in step xv is propylamine.

25. A method for preparing diphenyldiacetylene liquid crystal compounds as set forth in claim 10 wherein the inert atmosphere in step xv is an $N_2$ atmosphere.

* * * * *